US009155980B2

(12) United States Patent
Glad et al.

(10) Patent No.: US 9,155,980 B2
(45) Date of Patent: Oct. 13, 2015

(54) SEPARATION MEDIUM FOR CHROMATOGRAPHY OF VARIOUS BIOMOLECULES

(71) Applicant: GE HEALTHCARE BIO-SCIENCES AB, Uppsala (SE)

(72) Inventors: Gunnar Glad, Uppsala (SE); Bo-Lennart Johansson, Uppsala (SE); Jean-Luc Maloisel, Uppsala (SE); Nils Norrman, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 295 days.

(21) Appl. No.: 13/771,302

(22) Filed: Feb. 20, 2013

(65) Prior Publication Data
US 2013/0153499 A1 Jun. 20, 2013

Related U.S. Application Data

(63) Continuation of application No. 13/002,878, filed as application No. PCT/SE2009/050666 on Jun. 4, 2009, now abandoned.

(30) Foreign Application Priority Data

Jul. 8, 2008 (SE) ...................................... 0801640

(51) Int. Cl.
*B01D 15/38* (2006.01)
*B01D 15/36* (2006.01)
*B01J 20/28* (2006.01)
(Continued)

(52) U.S. Cl.
CPC ............ *B01D 15/3828* (2013.01); *B01D 15/36* (2013.01); *B01J 20/285* (2013.01); *B01J 20/286* (2013.01); *B01J 20/28092* (2013.01); *B01J 20/3242* (2013.01); *B01J 20/3293* (2013.01);
(Continued)

(58) Field of Classification Search
CPC .. B01D 15/36; B01D 15/3828; B01D 15/166; B01J 20/28092; B01J 20/285; B01J 20/286; B01J 20/3293; B01J 20/3242; C07K 1/16; C07K 1/22; C07K 16/00
USPC ................... 210/635, 656, 659, 198.2, 502.1; 530/413, 416, 417
See application file for complete search history.

(56) References Cited

U.S. PATENT DOCUMENTS 5,436,161 A 7/1995 Bergstrom et al.
6,426,315 B1 7/2002 Bergstrom et al.
(Continued)

OTHER PUBLICATIONS

Lakhiari, H., et al., Journal of Chromatography B, 818 (2005) 53-59.
(Continued)

*Primary Examiner* — Ernest G Therkorn
(74) *Attorney, Agent, or Firm* — Parks Wood LLC

(57) ABSTRACT

The present invention relates to a separation medium, comprising an inner core of a porous material provided with charged ligands, and an outer lid comprising a porous material provided with charged ligands, wherein the charge of the ligands in the inner core is opposite that of the charge of the ligands in the lid. The present invention also relates to a method for biomolecule separation comprising applying a sample to the above separation medium, wherein large molecules are prevented from entering the medium by charge repulsion from the medium and small molecules are captured in the inner core.

11 Claims, 1 Drawing Sheet

(51) Int. Cl.
*B01J 20/285* (2006.01)
*B01J 20/286* (2006.01)
*B01J 20/32* (2006.01)
*C07K 1/16* (2006.01)
*C07K 1/22* (2006.01)
*C07K 16/00* (2006.01)
*B01D 15/16* (2006.01)

(52) U.S. Cl.
CPC ... *C07K 1/16* (2013.01); *C07K 1/22* (2013.01); *C07K 16/00* (2013.01); *B01D 15/166* (2013.01)

(56) References Cited

U.S. PATENT DOCUMENTS

| | | |
|---|---|---|
| 6,852,230 B2 | 2/2005 | Belew et al. |
| 2005/0196856 A1 | 9/2005 | Harrold et al. |
| 2007/0125711 A1 | 6/2007 | Bergstrom et al. |
| 2007/0212540 A1 | 9/2007 | Cheng et al. |

OTHER PUBLICATIONS

Serres, A., et al., Journal of Chromatography A, 711 (1995) 151-157.

SEPARATION MEDIUM FOR CHROMATOGRAPHY OF VARIOUS BIOMOLECULES

CROSS-REFERENCE TO RELATED APPLICATIONS

This application is a continuation filing of U.S. patent application Ser. No. 13/002,878 filed Jan. 6, 2011, now abandoned, which is a filing under 35 U.S.C. §371 and claims priority to international patent application number PCT/SE2009/050666 filed Jun. 4, 2009, published on Jan. 14, 2010 as WO 2010/005364, which claims priority to application number 0801640-4 filed in Sweden on Jul. 8, 2008.

FIELD OF THE INVENTION

The present invention relates to a novel separation medium intended for chromatography of various biomolecules. The separation medium has an inner core and a lid which are differently charged. Large molecules are separated from the medium by charge repulsion and small molecules are eluted from inner core of the separation medium.

BACKGROUND OF THE INVENTION

Within biotechnology, one of the most widely used separation methods is chromatography. The term chromatography embraces a family of closely related separation methods. The feature distinguishing chromatography from most other physical and chemical methods of separation is that two mutually immiscible phases are brought into contact wherein one phase is stationary and the other mobile. The sample mixture, introduced into the mobile phase, undergoes a series of interactions i.e. partitions between the stationary and mobile phases as it is being carried through the system by the mobile phase. Interactions exploit differences in the physical or chemical properties of the components in the sample. These differences govern the rate of migration of the individual components under the influence of a mobile phase moving through a column containing the stationary phase. Separated components emerge in a certain order, depending on their interaction with the stationary phase. The least retarded component elutes first, the most strongly retained material elutes last. Separation is obtained when one component is retarded sufficiently to prevent overlap with the zone of an adjacent solute as sample components elute from the column.

The chromatographic methods suggested up to date are based on different modes of interaction with a target. Thus, for example, in ion-exchange chromatography, the functional groups are permanently bonded ionic groups with their counter ions of opposite charge, while in hydrophobic interaction chromatography (HIC), the interaction between the stationary phase and the component to be separated is based on hydrophobicity. Other chromatographic separation principles are well known to the skilled person in the art.

The stationary phase, also known as the separation matrix, comprises a support, which is commonly a plurality of essentially spherical particles, and ligands coupled to the support. In most separation matrices, the support is porous to allow a larger amount of ligand and consequently more bound target compound in each particle. The support is most often a natural or synthetic polymer and the spherical particles may be produced in a number of different ways. Natural polymers often used for this purpose are the polysaccharides dextran and agarose.

For separation of biomolecules, by chromatographic and batch-wise procedures, the porosity of the beads is very important. One advantage of polymeric media is the opportunity of pore size variation over broad ranges. A general rule, which is accepted throughout the literature, is to use media with large pore sizes for large molecules.

It would be desirable to have alternative ways of separating large molecules without having to use large porosity and which are not limited to separation of large molecules but may also be used to separate molecules of any size.

SUMMARY OF THE INVENTION

The present invention provides novel media and methods for separation of large as well as small biomolecules which combines several separation principles and parameters into one and the same medium.

In a first aspect, the invention provides a separation medium, comprising an inner core of a porous material provided with charged ligands, and an outer lid comprising a porous material provided with charged ligands, wherein the charge of the ligands in the inner core is opposite that of the charge of the ligands in the lid.

If the ligands in the core are negatively charged then the ligands in the lid are positively charged, and vice versa.

The porous material is preferably a sieving material, such as a gel filtration material commonly used for chromatography.

The porous material in the inner core may have the same porosity as the porous material in the lid. In this case the amount of charged ligands is higher in the lid than in the core. The ligand density in the lid should be >10%, such as >25% or >50% or >100%, of the ligand density in the core.

The separation medium may be designed for any type of biomolecule(s) and/or portions thereof.

Preferably, the porosity of the lid and the inner core allows penetration of a biomolecule with a molecular weight of less than approximately 100 000 g/mol. This limit is very useful for separation of relatively large molecules, such as MAbs, which do not enter the inner core but are obtained in the flow through if a column format is used. The separation medium may be used in any format, such as a column format or batch format. The porosity may be chosen to exclude molecules of certain sizes or weights and to allow penetration of those molecules that are smaller and/or lighter than these. The invention is not restricted to any specific porosity ranges, on the contrary, the porosity of the lid and inner core is to be decided in dependence on the size and or molecular weight of the biomolecule(s) intended to be purified.

In another embodiment the porosity of the inner core and lid allows penetration of a biomolecule with a molecular weight of less than 50 000 g/mol. This limit may be very useful for separation of small molecules which have entered the inner core and may be eluted therefrom.

In an alternative embodiment, the porous material in the inner core has the larger porosity than the porous material in the lid. For example, the porosity of the lid is such that biomolecules larger or equal to a molecular weight of 20 000, preferably 50 000 or 100 000 g/mol are excluded, and the porosity of the inner core is larger than the lid porosity.

The porous material is derived from a synthetic polymer material, such as styrene or styrene derivatives, divinylbenzene, acrylamides, acrylate esters, methacrylate esters, vinyl esters and vinylamides, or from a natural polymer material, such as carbohydrate material selected from agarose, agar, cellulose, dextran, chitosan, konjac, carrageenan, gellan and alginate.

The charged ligands may be selected from, for example are —$SO_3^-$, —$COO^-$, —$N^+(CH_3)_3$ or —$NH^+(C_2H_5)_2$ In a second aspect, the invention relates to a method for biomolecule separation comprising applying a sample to the above described separation medium, wherein large molecules are prevented from entering the medium by charge repulsion from the medium and small molecules are captured in the inner core.

In this case, the charge repulsion is caused by the charged ligands in the lid.

The charge repulsion, and thereby the prevention of entering of large molecules, may be accompanied by a lower porosity (=steric hindrance) in the lid compared to the inner core.

In the method according to the invention large molecules are obtained in the flow through by charge repulsion and small molecules adsorbed in the inner core are eluted from the separation medium.

The small molecules may be eluted with a salt gradient. A typical desorption means that ionic strength is increased compared to that used during adsorption and in many cases corresponds to at least 0.4-0.6 M NaCl.

Alternatively, the small molecules are eluted with a salt gradient and/or a pH gradient, in such a way that a portion of the small molecules gradually adhere to the ligands in the lid on their way out from the separation medium.

The method may be run in any column format and the desired biomolecules may be obtained in the flow-through. This is the case when it is desired to purify or separate large molecules such as cells, cell particles, virus, plasmids or immunoglobulins. The method is especially suitable for MAb purification.

The method may be run in column format and the desired molecules may be obtained by elution from the inner core of the separation medium. This is the case when it is desired to purify or separate small molecules such as small proteins and peptides. The method is especially suitable for biomarker purification.

DETAILED DESCRIPTION OF THE INVENTION

The present invention may be used for separation of humanized monoclonal antibodies (mAbs) which hold significant promise as biopharmaceuticals. One of the most challenges faced in the purification of mAbs is their separation from host cell proteins (HCPs) in the cell culture media.

The separation medium according to the invention may be used for separation of almost any molecule but will be exemplified by a medium having a lid and an inner core wherein said medium maximizes the HCPs interaction and minimizes the interaction between the IgG molecules (monoclonal antibodies) and the core-ligands. This was accomplished by modification of chromatography beads with a charge repulsion lid or a lid composed of both a "gel filtration lid" and a charge repulsion lid. This new chromatography medium of the invention makes it possible to apply adsorption conditions so that most of the HCPs interact with core-ligands.

Figure 1:
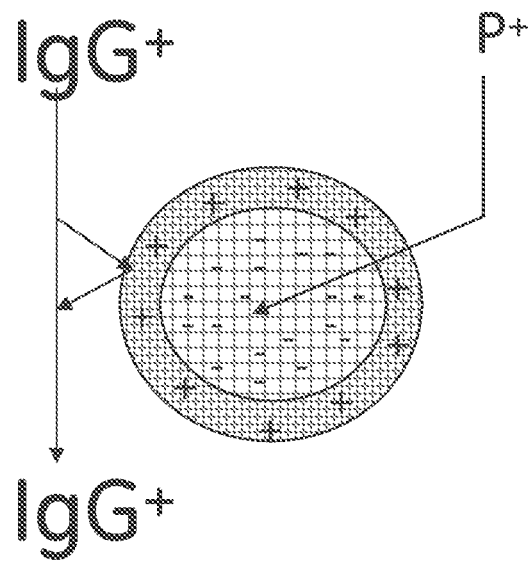
FIG. 1 shows a schematic illustration of the chromatographic properties and the construction of SEPHAROSE™ 6 Fast Flow bead with a DEAE-dextran lid and a negatively charged ligand in the core of the bead. P is host cell proteins and IgG is human immunoglobulin.

In FIG. 1 is a schematic illustration of a bead constructed with a lid comprised of both a gel filtration lid and a positively charged ligand. To accomplish charge repulsion the mobile phase must be adjusted to a pH-value where the monoclonal antibodies are positively charged (FIG. 1). Furthermore, the interior of the beads are occupied with core-ligands that are negatively charged (FIG. 1). This means that the host cell proteins also must be positively charged to be able to interact with the negatively charged core ligands. With the construction presented in FIG. 1 IgG is hindered to penetrate into the beads by charge repulsion and a steric effect (due to smaller pore sizes in the lid compare to the pore sizes in the core of the beads).

Figure 2:
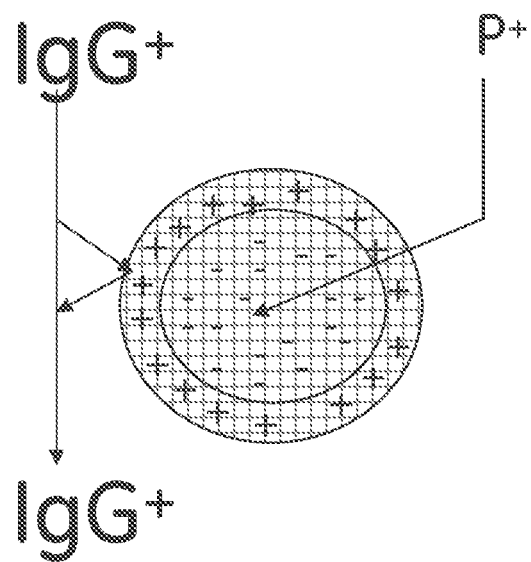
FIG. 2 is a schematic illustration of the chromatographic properties and the construction of SEPHAROSE™ 6 Fast Flow bead with positively charged groups (—$N^+(CH_3)_3$— prototype Q) in the lid and a negatively charged ligand (—$SO_3^-$) in the core of the bead. P is host cell proteins and IgG is human immunoglobulin.

In FIG. 2 is a bead construction depicted that excludes IgG to penetrate the core of the bead only by charge repulsion. The pore size distribution of the bead means that IgG can penetrate into the core of the bead but the charge repulsion lid prevent this to happen. The charge repulsion lid is designed in a way that smaller proteins than IgG are not influenced by charge repulsion and will therefore have access to the interior of the beads.

EXAMPLES

The present examples are provided for illustrative purposes only, and should not be construed as limiting the scope of the present invention as defined by the appended claims. All references given below and elsewhere in the present specification are hereby included herein by reference.

Preparation of Charge Repulsion Media Based on Sepharose™ 6 Fast Flow and Designed for Capture of Host Cell Proteins General Volumes of matrix refer to settled bed volume.

Weights of matrix given in gram refer to suction dry weight. It is understood that these matrices are still water solvated material. For large scale reaction stirring is referring to a suspended, motor-driven stirrer since the use of magnet bar stirrer is prompt to damage the beads. Small-scale reactions (up to 20 mL of gel) were performed in closed vials and stirring refers to the use of a shaking table.

Conventional methods were used for the analysis of the functionality and the determination of the degree of allylation, epoxidation, or the degree of substitution of ion exchanger groups on the beads.

Two different ways to prepare a separation matrix according to the invention are exemplified below, starting from a cross linked agarose gel (SEPHAROSE™ 6 Fast Flow, GE Healthcare, Uppsala, Sweden).

Example 1

Preparation of DEAE Dextran Lid Prototypes (DEAE-DX1, DEAE-DX2 and DEAE-DX3) Based on SEPHAROSE™ 6 Fast Flow Preparation of DEAE Dextran Lid Allyl Activation of SEPHAROSE™ 6 Fast Flow.

SEPHAROSE™ 6 Fast Flow was washed with distilled water on a glass filter. The gel, 100 mL, was drained on the filter and weighed into a 3-necked round bottomed flask. NaOH (50 mL, 50%-solution) was added and mechanical stirring started. Sodium borohydride, 0.4 g, and sodium sulphate, 11.4 g, were added to the flask and the slurry heated to 50° C. on a water bath. After approximately one hour, 100 mL of allyl glycidyl ether (AGE) was added. The slurry was then left under vigorously stirring over night. After about 20 hours the slurry was transferred to a glass filter and the pH adjusted to around 7 with acetic acid (60%). The gel was then washed with distilled water (×4), ethanol (×4) and distilled water (×4). The allyl content was then determined by titration; 270 μmol/mL.

Partial Bromination.

Allylated gel, 41 mL, was weighed into a flask and 260 mL of distilled water and 0.5 g sodium sulphate was added. 0.53 equivalents of bromine, 300 μl, were then added with a pipette during vigorous stirring. After approximately 5 minutes (when the bromine had been consumed) the gel was washed with distilled water on a glass filter.

Coupling of DEAE-Dextran in the Lid.

10 mL portions of the partially brominated gel were transferred to flasks and mixed with DEAE-dextran solutions (see below). DEAE-dextran was obtained from GE Healthcare, Uppsala, Sweden. Three prototypes with different amount of DEAE-dextran applied were constructed:

Prototype DEAE-DX1: 7.2 g DEAE-Dextran in 15 mL of water.
Prototype DEAE-DX2: 6.0 g DEAE-Dextran in 15 mL of water.
Prototype DEAE-DX3: 4.8 g DEAE-Dextran in 15 mL of water.

To each slurry 2 g of NaOH and 0.1 g NaBH$_4$ were added. The slurries were heated to 50° C. and left stirring over night. After approximately 18 hours the pH was adjusted to approximately 7 with acetic acid (60% solution). The gel was then washed with distilled water on a glass filter. The amount of DEAE-dextran attached (estimated by measure the dry weight before and after coupling of DEAE-dextran) to the prototypes are presented in Table 1 (see the section chromatographic evaluation).

Core Coupling

Coupling of —SO$_3^-$ Groups in the Core of the Beads.

10 mL of DEAE-DX prototype (see above) were put with distilled water into a beaker and vigorous overhead stirring was begun. Bromine was added until the slurry had a remaining deeply orange/yellow colour. After 10 minutes of stirring sodium formiate (approximately 1.5 g) was added until the slurry was completely discoloured. The gel was then washed with distilled water on a glass filter.

Drained brominated gel was transferred to a flask with 4 g of sodium sulphite, dissolved in 10 mL of 2 M NaOH. The mixture was then left stiffing in 50° C. over night. After 20 hours the gel was washed with distilled water on a glass filter.

Example 2

Preparation of Prototype Q Based on SEPHAROSE™ 6 Fast Flow

Preparation of Q (—N$^+$(CH$_3$)$_3$-Groups) Lid
Allyl Activation of SEPHAROSE™ 6 Fast Flow.

SEPHAROSE™ 6 Fast Flow was washed with distilled water on a glass filter. The gel, 100 mL, was drained on the filter and weighed into a 3-necked round bottomed flask. NaOH (50 mL, 50%-solution) was added and mechanical stirring started. Sodium borohydride, 0.4 g, and sodium sulphate, 11.4 g, were added to the flask and the slurry heated to 50° C. on a water bath. After approximately one hour, 100 mL of AGE was added. The slurry was then left under vigorously stiffing over night. After about 20 hours the slurry was transferred to a glass filter and the pH adjusted to around 7 with acetic acid (60%). The gel was then washed with distilled water (×4), ethanol (×4) and distilled water (×4). The allyl content was then determined by titration; 270 μmol/mL.

Partial Bromination.

Allylated gel, 41 mL, was weighed into a flask and 260 mL of distilled water and 0.5 g sodium sulphate was added. 0.53 equivalents of bromine, 300 μl, were then added with a pipette during vigorous stirring. After approximately 5 minutes (when the bromine had been consumed) the gel was washed with distilled water on a glass filter.

Q-Coupling (Trimethyl Ammonium Chloride, TMA-Chloride).

10 mL of the partially brominated SEPHAROSE™ 6 Fast Flow was transferred to a flask and mixed with 5 mL of TMA-chloride solution. 5 mL of 2 M NaOH was then added and the slurry was heated to 50° C. and left stirring over night. After approximately 18 hours the pH was adjusted to approximately 7 with acetic acid (60% solution). The gel was then washed with distilled water on a glass filter. The total amount of coupled TMA-groups was determined by chloride titration and the Cl$^-$ capacity was estimated to 105 μmol/mL Core Coupling Coupling of —SO$_3^-$ Groups in the Core of the Beads.

10 mL of the Q-lid prototype (see above) were put with distilled water into a beaker and vigorous overhead stirring was begun. Bromine was added until the slurry had a remaining deeply orange/yellow colour. After 10 minutes of stirring sodium formiate (approximately 1.5 g) was added until the slurry was completely discoloured. The gel was then washed with distilled water on a glass filter.

Drained brominated gel was transferred to a flask with 4 g of sodium sulphite, dissolved in 10 mL of 2 M NaOH. The mixture was then left stirring in 50° C. over night. After 20 hours the gel was washed with distilled water on a glass filter.

Experiment 3

Chromatographic Evaluation of the Four Prototypes (DEAE-DX1, DEAE-DX2, DEAE-DX3 and Q)

The charge repulsion lid media to be investigated (Prototypes: DEAE-DX1, DEAE-DX2, DEAE-DX3 and Q), with respect to breakthrough capacity, were packed in HR 5/5 columns and the sample solution was pumped at a flow rate of 0.3 mL/min through the column after equilibration with buffer solution. The breakthrough capacity was evaluated at 10% of the maximum UV detector signal (280 nm). The maximum UV signal was estimated by pumping the test solution directly into the detector. The breakthrough capacity at 10% of absorbance maximum ($Q_{b10\%}$) was calculated according to the formula:

$$Q_{b10\%} = (T_{R10\%} - T_{RD}) \times C/V_c$$

where $T_{R10\%}$ is the retention time (min) at 10% of absorbance maximum, $T_{RD}$ the void volume time in the system (min), C the concentration of the sample (4 mg protein/mL) and $V_c$ the column volume (mL). The adsorption buffer used at breakthrough capacity measurements was 50 mM acetate (pH 4.0).

Sample

The samples used were human immunoglobulin (IgG, Gammanorm), bovine serum albumin (BSA), ovalbumin and lysozyme. The proteins were dissolved in the adsorption buffers at a concentration of 4 mg/mL and only one protein at a time was applied into the column.

Instrumental
Apparatus
LC System: ÄKTAexplorer 10 XT or equal
Software: UNICRON™
Column: HR 5/5
Instrument Parameters
Flow rate: 0.3 mL/min
Detector cell: 10 mm
Wavelength: 280 nm
UNICORN™ Method
The main method used is depicted below:
0.00 Base CV 1.00 {mL} #Column volume {mL} Any
0.00 Block Start Conditions
    0.00 Base SameAsMain
    0.00 Wave length 280 {nm} 254 {nm} 215 {nm}
    0.00 AvaragingTime 2.56 {sec}
    0.00 Alarm Pressure Enable 3.00 {MPa} 0.00 {MPa}
    0.00 End Block
0.00 Block Column Position
0.00 Block Equilibration
    0.00 Base SameAsMain
    0.00 PumpAInlet A1
    0.00 BufferValveA1 A11
    0.00 Flow 0.3 {mL/min}
    1.00 Set Mark ( )#column name
    3.9 AutoZeroUV
    5.0 #Equilibration volume End Block
0.00 Block Sample Loading
    0.00 Base volume
    0.00 Flow (1)#flow rate {mL/min}
    0.00 Set Mark ( )#sample
    0.00 InjectionValve Inject
    0.00 Watch UV Greater Than (100) #20 percent maxabs {mAu} END BLOCK
    49.00 InjectionValve Load
    49.00 End Block
0.00 Block Column Wash
    0.00 Base SameAsMain
    0.00 InjectionValve Load
    0.00 Watch Off UV
    0.00 PumpAInlet A1
    0.00 BufferValveA1 A11
    0.00 Watch UV Less Than (20) #5 percent {mAu} END BLOCK
    20.00 End Block
0.00 Block Gradient Elution
    0.00 Base SameAsMain
    0.00 PumpBInlet B1
    0.00 Gradient 100 {% B} 2.00 {base}
    0.00 Flow 0.30 {mL/min}
    10.00 Gradient 0.00 {% B} 0.00 {base}
    10.00 End Block
0 Block Reequilibration
    0.00 End Method
Results and Discussion The base matrix used for the different prototypes where SEPHAROSE™ 6 Fast Flow. The fractionation range of SEPHAROSE™ 6 Fast Flow for globular proteins is $1 \times 10^4$-$4 \times 10^6$ according to the manufacture (GE Healthcare, Uppsala, Sweden). This means that human immunoglobulin and smaller proteins can diffuse into the beads. However, this invention has proved that human immunoglobulin can be selectively be hindered to diffuse into the beads by charge repulsion lid and a combination of charge repulsion and a "gel filtration lid" (FIGS. 1 and 2) while smaller proteins have access to the interior of the beads.

Three different prototypes (DEAE-DX1, DEAE-DX2, DEAE-DX3) with a lid composed of charged dextran (DEAE dextran) have been tested and all three prototypes were substituted with $—SO_3^-$ groups in the core of the beads (FIG. 1). Different amounts of DEAE dextran was tested (Table 1) in order to accomplish charge repulsion and a gel filtration lid for large positively charged molecules (IgG) while smaller positively charged proteins are allowed to penetrate the lid. To test if attachment of only positively charged groups ($—N^+(CH_3)_3$) in the lid segment can hinder IgG to diffuse into the SEPHAROSE™ 6 Fast Flow beads the Q-prototype was produced (FIG. 2 and Table 1). This prototype was also substituted with $—SO_3^-$ groups in the core of the beads (FIG. 2).

TABLE 1

The amount of ligands coupled in the lid and the ion exchange capacity in the core for DEAE-dextran lid prototypes (FIG. 1) and for one prototype with Q-groups ($—N^+(CH_3)_3$) in the lid (FIG. 2).

| Prototype | Lid concentration | $—SO_3^-$ conc. in the core |
|---|---|---|
| DEAE-DX1 | 37 mg/mL | 80 μmol/mL |
| DEAE-DX2 | 34 mg/mL | 71 μmol/mL |
| DEAE-DX3 | 24 mg/mL | 71 μmol/mL |
| Q | 105 μmol/mL | 80 μmol/mL |

The breakthrough capacity of all four prototypes (DEAE-DX1-3 and Q) was determined for a number of proteins (IgG, BSA, ovalbumin and lysozyme). The molecular weight of the proteins is shown in Table 2. The mobile phase used (50 mM acetate, pH 4.0) means that all investigated proteins are positively charged (the isoelectric point of the proteins is presented in Table 2).

TABLE 2

Molecular weight of the proteins used for breaktrough determination.

| Protein | Molecular weight (g/mol) | Isoelectric point |
|---|---|---|
| IgG | 150 000 | 5.5 |
| BSA | 68 000 | 5.1 |
| Ovalbumin | 43500 | 4.7 |
| Lactalbumin | 14400 | 5.2 |

The results from the breakthrough measurements are presented in Table 3 and the prototype DEAE-DX3, with the lowest amount of dextran in the lid (24 mg/mL), resulted in low breakthrough capacity of IgG but relatively high for the other investigated proteins (Table 3). Table 3 also shows that a higher amount of DEAE dextran (prototypes DEAE-DX1-2) in the lid resulted in a low capacity of both IgG and BSA. Prototype DEAE-DX1 with the highest content of DEAE-dextran in the lid resulted also in a low breakthrough capacity of ovalbumin. The result clearly shows that IgG can be excluded from entering the beads by a lid composed of DEAE-dextran. High amounts of DEAE-dextran in the lid can be used to exclude smaller proteins such as BSA and ovalbumin. To test if only charge repulsion effects can exclude IgG from entering the beads prototype Q was designed (FIG. 2). Prototype Q with ($—N^+(CH_3)_3$) in the lid segment (no dextran) gave very low breakthrough capacity of IgG and high capacities of the other proteins (Table 3).

TABLE 3

Breakthrough capacity of IgG, BSA, ovalbumin and lysozyme for three prototypes (DEAE-DX1-3) composed of a DEAE dextran lid and —$SO_3^-$ groups in the core of the beads (SEPHAROSE ™ 6 Fast Flow) and one prototype (Q) with a charged lid composed of —$N^+(CH_3)_3$- groups (no dextran) and —$SO_3^-$ groups in the core of the beads.

| Prototype | Breakthrough capacity (mg/mL) | | | |
|---|---|---|---|---|
| | IgG | BSA | Ovalbumin | Lysozyme |
| DEAE-DX1 | 0 | 0.1 | 1 | 8 |
| DEAE-DX2 | 0 | 0.2 | 15 | 36 |
| DEAE-DX3 | 0.5 | 12 | 34 | 52 |
| Q | 2.7 | 32 | 41 | 56 |

Even though the present invention has been described above in terms of specific embodiments, many modification and variations of this invention can be made as will be obvious to those skilled in the art, without departing from its spirit and scope as set forth in the following claims.

What is claimed is:

1. A method for separation of first and second biomolecules comprising:
    charging a sample comprising the first and second biomolecules, where the second biomolecules are larger than the first biomolecules, so that the first and second biomolecules have a charge; and
    applying the sample to a separation medium comprising an outer lid and an inner core positioned within the outer lid,
    wherein the outer lid comprises ligands charged the same as the first and the second biomolecules and has a first porosity smaller than the second biomolecules,
    wherein the inner core comprises ligands charged opposite the first and the second biomolecules and has a second porosity smaller than the second biomolecules,
    wherein the second biomolecules are charge repulsed from the separation medium, and
    wherein the first porosity and the second porosity allow penetration of the first biomolecules but not the second biomolecules into the inner core.

2. The method of claim 1, wherein the first porosity is smaller than the second porosity preventing entry of the second biomolecules through the first porosity.

3. The method of claim 1, wherein the second biomolecules are obtained in column flow-through by charge repulsion and the first biomolecules are charge attracted into the inner core and then eluted from the separation medium.

4. The method of claim 3, wherein the first biomolecules are eluted with a salt gradient.

5. The method of claim 3, wherein the first biomolecules are eluted with a salt gradient or a pH gradient, such that a portion of the first biomolecules gradually adhere to the ligands in the outer lid as they are eluted from the inner core.

6. The method of claim 3, wherein the second biomolecules are obtained by elution from the inner core of the separation medium.

7. The method of claim 1, wherein the first and second porosities allow penetration of first biomolecules having a molecular weight of less than 100 000 g/mol.

8. The method of claim 7, wherein the first and second porosities allow penetration of the first biomolecules having a molecular weight of less than 50 000 g/mol.

9. The method of claim 1, wherein the outer lid has a higher ligand density than the inner core.

10. The method of claim 1, wherein the first porosity is larger than the second porosity preventing the second biomolecules entry through the first porosity.

11. The method of claim 1, wherein the second porosity is such that first biomolecules having a molecular weight approximately equal to or greater than 20 000 g/mol, preferably 50 000 or 100 000 g/mol, are excluded.

* * * * *